(12) United States Patent
Shinohara et al.

(10) Patent No.: US 8,409,594 B2
(45) Date of Patent: Apr. 2, 2013

(54) SOLID OIL-IN-WATER EMULSION

(75) Inventors: Shigeo Shinohara, Otsu (JP); Fumiki Harano, Otsu (JP); Shinji Tsujimoto, Osaka (JP); Isamu Saeki, Tondabayashi (JP)

(73) Assignee: Otsuka Pharmaceutical Co., Ltd., Tokyo (JP)

( * ) Notice: Subject to any disclaimer, the term of this patent is extended or adjusted under 35 U.S.C. 154(b) by 247 days.

(21) Appl. No.: 11/722,965

(22) PCT Filed: Dec. 27, 2005

(86) PCT No.: PCT/JP2005/023865
§ 371 (c)(1),
(2), (4) Date: Jun. 27, 2007

(87) PCT Pub. No.: WO2006/070789
PCT Pub. Date: Jul. 6, 2006

(65) Prior Publication Data
US 2007/0280979 A1 Dec. 6, 2007

(30) Foreign Application Priority Data

Dec. 28, 2004 (JP) .................................. 2004-381162

(51) Int. Cl.
*A61K 8/06* (2006.01)
*A61K 8/92* (2006.01)
*A61K 31/7076* (2006.01)
*A61K 8/67* (2006.01)
*A61K 8/34* (2006.01)
*A61K 8/37* (2006.01)
*A61Q 1/06* (2006.01)
*A61Q 19/00* (2006.01)

(52) U.S. Cl. .......... 424/401; 424/400; 514/47; 514/772; 516/21

(58) Field of Classification Search ........................ None
See application file for complete search history.

(56) References Cited

U.S. PATENT DOCUMENTS 5,763,497 A * 6/1998 Ikeda et al. ................... 424/401

FOREIGN PATENT DOCUMENTS

| CN | 1344149 A | 4/2002 |
|---|---|---|
| CN | 1476318 A | 2/2004 |
| EP | 1 342 462 A1 | 9/2003 |
| EP | 1342462 A1 * | 9/2003 |
| JP | 6-321731 A | 11/1994 |
| JP | 8-245363 A | 9/1996 |
| JP | 8-291021 A | 11/1996 |
| JP | 9-157153 A | 6/1997 |
| JP | 9-194330 A | 7/1997 |
| JP | 9-194331 A | 7/1997 |
| JP | 10-291914 A | 11/1998 |
| JP | 2003-95862 A | 4/2003 |
| JP | 2003-113034 A | 4/2003 |
| JP | 2004-91399 A | 3/2004 |
| JP | 2004-238386 A | 8/2004 |
| JP | 3565332 B2 | 9/2004 |
| WO | WO 2004016238 A1 * | 2/2004 |

OTHER PUBLICATIONS

Sodium Carboxymethylcellulose. Aqualon® Technical Brochure. Revised Apr. 2002.*
Carbopol® Polymers. LubrizolTM Technical Data Sheet 103. Jan. 2002 Edition.*
Lipstick. Harry's Cosmeticology. 8th Edition (2000), pp. 543-551.*
Office Action dated May 8, 2009 in corresponding Chinese Application with English translation.

* cited by examiner

*Primary Examiner* — David J Blanchard
*Assistant Examiner* — Peter Anthopolos
(74) *Attorney, Agent, or Firm* — Finnegan, Henderson, Farabow, Garrett & Dunner, L.L.P.

(57) ABSTRACT

The present invention aims to provide solid compositions comprising an oil-in-water emulsion that have sufficient hardness and good feel when used, and can sufficiently exhibit the physiological functions of an electrolyte. A solid composition is obtained by preparing an oil-in-water emulsion by combining a solid oil (A), a liquid oil (B), a surfactant (C), a polyhydric alcohol (D), an electrolyte (E), and water (F).

18 Claims, 1 Drawing Sheet

SOLID OIL-IN-WATER EMULSION

TECHNICAL FIELD

The present invention relates to a solid oil-in-water emulsion. More specifically, the present invention relates to a solid composition comprising an oil-in-water emulsion that stably maintains its solid state even though an effective concentration of electrolyte with physiological functions is contained, has a good feel when used, and can sufficiently develop physiological functions of the electrolyte.

BACKGROUND OF THE INVENTION

As prior-art solid cosmetic materials containing moisture, water-in-oil emulsions containing liquid oil, solid oil, water, and a lipophilic surfactant are generally used (e.g., Patent Document 1). However, water-in-oil emulsions pose a problem that electrolytes, particularly water soluble or hydrophilic substances that exert physiological functions when applied to the skin, cannot exhibit the functions effectively. This is because, in water-in-oil emulsions, the aqueous phase in which the electrolyte as an active ingredient is dissolved is enclosed by the oil phase and therefore it is difficult to bring the electrolyte into contact with the skin.

In contrast, oil-in-water emulsions have, on the exterior, an aqueous phase in which an electrolyte having physiological functions is dissolved, which improves the permeability of the electrolyte in the skin. Thus, such electrolytes having physiological functions are preferably formulated into oil-in-water emulsions as solid preparations. Heretofore, solid compositions comprising an oil-in-water emulsion are already known. For example, the following are reported: solid cosmetics comprising an oil-in-water emulsion having a surfactant, oil, and β-1,3-glucan (Patent Document 2); solid cosmetics comprising an oil-in-water emulsion having water, specific wax ester, an amphoteric surfactant, titanium oxide of a specific shape, and higher fatty acid (Patent Document 3); solid cosmetics comprising an oil-in-water emulsion having agar and/or gelatin, polyethylene glycol, an oil, and water (Patent Document 4).

However, oil-in-water emulsions are disadvantageous in that when the electrolyte is dissolved in the aqueous phase, the emulsion cannot form a gel, which results in that the emulsion cannot solidify or cannot maintain sufficient hardness. In addition, in some case, oil-in-water emulsions have another disadvantage that physiological functions of an electrolyte dissolved in the aqueous phase cannot be sufficiently exhibited. The above-described disadvantages are obvious particularly when a purine base, its salt, or a water soluble vitamin is used as an electrolyte. The inventors confirmed that the disadvantages tend to become prominent particularly when a specific amount of purine base or its salt is used in combination with a specific amount of water soluble vitamin.

In the present circumstances, since the above-described disadvantages have not been overcome, practical use of solid compositions comprising an oil-in-water emulsion having an effective concentration of electrolyte with physiological functions has not yet been achieved. In view of the above-described prior-art techniques, it has been demanded to develop solid compositions comprising an oil-in-water emulsion that have sufficient hardness and good feel when used, and can sufficiently exhibit the physiological functions of an incorporated electrolyte.

[Patent Document 1] Japanese Unexamined Patent Publication No. H6 (1994)-321731
[Patent Document 2] Japanese Unexamined Patent Publication No. H8 (1996)-291021
[Patent Document 3] Japanese Unexamined Patent Publication No. H9 (1997)-194331
[Patent Document 4] Japanese Unexamined Patent Publication No. 2003-95862

DISCLOSURE OF THE INVENTION

Problem to be Solved by the Invention

The present invention aims to provide solid compositions comprising an oil-in-water emulsion that have sufficient hardness and good feel when used, and can sufficiently exhibit the physiological functions of an electrolyte. In particular, the present invention aims to provide solid compositions comprising an oil-in-water emulsion that have a good feel when used while holding its stable solid state, and can effectively demonstrate an action of preventing skin pigmentation, although the composition comprises a purine base, its salt, or a water soluble vitamin in effective concentrations.

Means for Solving the Problem

The present inventors conducted extensive research to achieve the above object, and found that a solid composition that has sufficient hardness and good feel when used and that can sufficiently exhibit physiological functions of an electrolyte can be obtained by preparing an oil-in-water emulsion using a solid oil (A), liquid oil (B), surfactant (C), polyhydric alcohol (D), and water (E) together with an electrolyte (E). The present inventors also found that such a composition has a good feel when used while holding its stable solid state, and also effectively exhibits the physiological functions of these electrolytes when a purine base, its salt, or a water soluble vitamin is used as the electrolyte (E) and particularly when a purine base or its salt is used in combination with a water soluble vitamin. The present inventors made further improvements based on these findings, and accomplished the present invention.

More specifically, the invention provides the following solid compositions (solid oil-in-water emulsion compositions).

Item 1. A solid composition which is an oil-in-water emulsion comprising a solid oil (A), a liquid oil (B), a surfactant (C), a polyhydric alcohol (D), an electrolyte (E), and water (F).

Item 2. A solid composition according to item 1, wherein the electrolyte (E) is at least one selected from the group consisting of purine bases, water soluble vitamins, water soluble vitamin derivatives, and salts thereof.

Item 3. A solid composition according to item 1, wherein the electrolyte (E) is at least one selected from the group consisting of adenosine 3',5'-cyclic phosphoric acid, adenosine monophosphate, adenosine diphosphate, adenosine triphosphate, and salts thereof.

Item 4. A solid composition according to item 1 wherein the electrolyte (E) is a combination of at least one selected from the group (E-1) consisting of purine bases and salts thereof and at least one selected from the group (E-2) consisting of water soluble vitamins, water soluble vitamin derivatives, and salts thereof.

Item 5. A solid composition according to Item 1 wherein the electrolyte (E) is a combination of at least one selected from the group (E-1) consisting of adenosine 3',5'-cyclic phosphoric acids, adenosine monophosphates, adenosine diphosphates, adenosine triphosphates, and salts thereof and at least one selected from the group (E-2) consisting of ascorbic acids, ascorbic acid derivatives, and salts thereof.

Item 6. A solid composition according to item 1 wherein the electrolyte (E) is a combination of at least one selected from the group (E-1) consisting of adenosine monophosphates and salts thereof and at least one selected from the group (E-2) consisting of ascorbic acid 2-glucoside and salts thereof.

Item 7. A solid composition according to item 1 comprising 5 to 50% by weight of solid oil (A), 10 to 60% by weight of liquid oil (B), 1 to 20% by weight of surfactant (C), 5 to 30% by weight of polyhydric alcohol (D), 0.1 to 20% by weight of electrolyte (E), and 10 to 50% by weight of water.

Item 8. A solid composition according to item 1 wherein the composition is a cosmetic.

Item 9. A solid composition according to item 1 wherein the composition is an externally-applied pharmaceutical.

Item 10. A solid composition according to item 1 having a lipstick form.

Item 11. Use of a solid oil (A), a liquid oil (B), a surfactant (C), a polyhydric alcohol (D), an electrolyte (E), and water (F) for the production of a solid oil-in-water emulsion.

Item 12. Use of a solid oil (A), a liquid oil (B), a surfactant (C), a polyhydric alcohol (D), and water (F) for the production of a solid oil-in-water emulsion comprising at least one selected from the group consisting of purine bases, water-soluble vitamins, water-soluble vitamin derivatives, and salts thereof.

Item 13. Use of a solid oil (A), a liquid oil (B), a surfactant (C), a polyhydric alcohol (D), and water (F) for the production of a solid oil-in-water emulsion comprising at least one selected from the group (E-1) consisting of purine bases and salts thereof and at least one selected from the group (E-2) consisting of water soluble vitamins, water soluble vitamin derivatives, and salts thereof.

BRIEF DESCRIPTION OF THE DRAWINGS

In FIG. 1, the unit of the period (w) of a horizontal axis is a week (week).

BEST MODE FOR CARRYING OUT THE INVENTION

Figure 1:
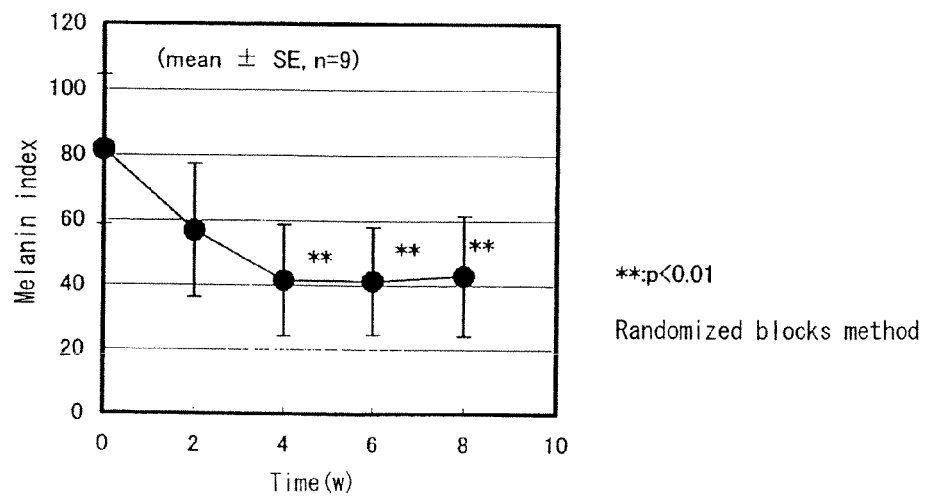
FIG. 1 is a graph showing the change with time in the melanin index when the lipstick obtained in Example 1 is applied to lips for 56 days.

Hereinafter, the present invention will be described in detail.

The solid composition of the invention is an oil-in-water emulsion comprising solid oil (A), liquid oil (B), surfactant (C), polyhydric alcohol (D), electrolyte (E), and water (F).

In the invention, the solid oil is an oily component that is solid or a semi-solid at normal temperature (25° C.). Various solid oils can be used without limitation as the solid oil (A) for the solid composition of the invention insofar as they are cosmetically or pharmacologically acceptable, but oils that are solid at normal temperature are preferable. Mentioned as examples of such solid oils are waxes, such as candelilla wax, carnauba wax, hydrogenated jojoba oil, rice bran wax, shellac, lanolin, yellow bees wax, spermaceti wax, montan wax, and the like; solid hydrocarbons, such as ozokerite, ceresin, paraffin, polyethylene wax, microcrystalline wax, vaseline, and the like; solid esters, such as myristyl myristate, cetyl palmitate, cetyl lactate, cholesteryl oleate, phytosteryl oleate, cholesteryl stearate, cholesteryl hydroxystearate, and the like. These solid oils may be used alone or in combination. Among the above, solid oils having melting points as high as 50° C. or higher, more preferably as high as 60° C. or higher, are preferable in terms of securing a stable solid state. In particular, the combinations of hydrogenated jojoba oil with other wax(es), solid hydrocarbon(s), or solid ester(s) are preferable. Among these combinations, the combination of hydrogenated jojoba oil and ceresin or the combination of hydrogenated jojoba oil and candelilla wax is the most effective. In the case of the combined use of hydrogenated jojoba oil with other wax(es), solid hydrocarbon(s), or solid ester(s), the content of other wax(es), solid hydrocarbon(s), or solid ester(s) is usually 50 to 1000 parts by weight, preferably 100 to 500 parts by weight, and more preferably 100 to 300 parts by weight based on 100 parts by weight of hydrogenated jojoba oil.

The content of the above-mentioned solid oil (A) in the solid composition of the invention is usually 5 to 50% by weight, preferably 10 to 40% by weight, and more preferably 15 to 30% by weight based on the total weight of the composition.

Various liquid oils can be used without limitation as the liquid oil (B) for the solid composition of the invention insofar as they are cosmetically or pharmacologically acceptable. Specific examples of such liquid oils (B) include liquid hydrocarbons, such as squalane, liquid paraffin, liquid isoparaffin, α-olefin oligomer, and the like; liquid esters, such as isopropyl myristate, octyldodecyl myristate, oleyl oleate, decyl oleate, 2-hexyl decyl isostearate, hexyl decyl dimethyloctanoate, isopropyl palmitate, hexyl laurate, butyl stearate, and the like; vegetable oils, such as avocado oil, almond oil, olive oil, sesame oil, sasanqua oil, safflower oil, soybean oil, castor oil, camellia oil, corn oil, rapeseed oil, rice bran oil, par chic oil, palm kernel oil, palm oil, sunflower seed oil, grapeseeds oil, cotton seed oil, and the like; animal oils, such as turtle oil, mink oil, egg yolk fatty oil, and the like; silicone oils, such as dimethylpolysiloxane, methylphenyl polysiloxane, methylhydrogen polysiloxane, octamethylcyclotetrasiloxane, and the like. These liquid oils may be used alone or in combination.

Preferable as the liquid oil (B) used in the invention are liquid hydrocarbon(s), liquid ester(s), and the combination thereof, and more preferable is the combination of liquid hydrocarbon(s) and liquid ester(s). In the case of the combined use of liquid hydrocarbon(s) with liquid ester(s) as the liquid oil (B), the mixing ratio thereof is not limited. For example, the content of liquid hydrocarbon(s) is preferably 30 to 250 parts by weight and more preferably 50 to 150 parts by weight based on 100 parts by weight of liquid ester(s).

The content of the above-mentioned liquid oil (B) in the solid composition of the invention is, for example, usually 10 to 60% by weight, preferably 15 to 50% by weight, and more preferably 15 to 30% by weight based on the total weight of the composition. The liquid oil(s) (B) is contained in the solid composition of the invention usually in a proportion of 25 to 600 parts by weight, preferably 50 to 400 parts by weight, and more preferably 65 to 200 parts by weight based on the total amount of 100 parts by weight of the solid oil(s) (A).

There is no limitation on the surfactant (C) used in the solid composition of the invention insofar as it is cosmetically or pharmacologically acceptable. Any of nonionic surfactants, anionic surfactants, cationic surfactants, and amphoteric surfactants can be used.

Specific examples of the nonionic surfactants used as the surfactant (C) include POE branched alkyl ethers, such as POE octyldodecyl ether and the like; POE alkyl ethers, such as POE oleyl ether, POE cetyl ether, and the like; sorbitan fatty-acid esters, such as sorbitan monooleate, sorbitan monoisostearate, and the like; POE sorbitan fatty acid esters, such as POE sorbitan monooleate, POE sorbitan monoisostearate, POE sorbitan monolaurate, and the like; glycerol fatty acid esters, such as lipophilic glycerol monooleate, lipophilic glycerol monostearate, and glycerol myristate; POE glycerol fatty acid esters, such as POE glycerol oleate, POE glycerol monostearate, and the like; POE alkyl aryl ethers, such as POE cholestanol ether and the like; POE hydrogenated castor oils, such as POE hydrogenated castor oil, POE hydrogenated castor oil isostearate, and the like; glycerol ethers, such as isostearyl glycerol ether and the like; polyglycerol fatty acid esters, such as polyglycerol monostearate, polyglycerol diisostearate, decaglycerol decastearate, and the like; sucrose fatty acid esters, such as sucrose oleate, sucrose palmitate, sucrose stearate, sucrose dilaurate, and the like; alkanolamide surfactants, such as lauric monoethanolamide, lauric diethanolamide, and the like; etc.

Specific examples of anionic surfactants used as the surfactant (C) include fatty acid salts, such as potassium stearate, triethanolamine stearate, and the like; alkyl sulfates, such as sodium cetyl sulfate and the like; POE alkyl ether sulfates, such as POE alkyl (12, 13) ether sulfate triethanolamine and the like; N-acyl methyl taurates, such as sodium myristoyl methyl taurine and the like; alkyl phosphates, such as diethanolamine cetylphosphate and the like; POE alkyl-phosphorates, such as POE sodium cetyl phosphate and the like; N-acylamino acid salts, such as sodium N-stearoyl-L-glutamate, potassium N-stearoyl-L-glutamate, triethanolamine N-stearoyl-L-glutamate, and the like; etc.

Specific examples of cationic surfactants used as the surfactant (C) include alkyl trimethylammonium chlorides, such as stearyl trimethylammonium chloride and the like; dialkyl dimethylammonium chlorides, such as distearyl dimethyl ammonium chloride and the like; benzalkonium chloride and the like; etc.

Specific examples of amphoteric surfactants used as the surfactant (C) include alkyl carboxymethyl hydroxyethyl imidazolinium betaine, such as 2-alkyl-N-carboxymethyl-N-hydroxyethyl imidazolinium betaine and the like; alkyl amidopropyl betaine, such as lauryl amidopropyl betaine and the like; alkyl hydroxysulfobetaine, such as lauryl hydroxysulfobetaine, and the like; etc.

In the solid composition of the invention, these surfactants may be used alone or in combination.

As the surfactant (C), nonionic surfactants are preferable, lipophilic glycerol monostearates, POE hydrogenated castor oil, sucrose stearate, and polyglycerol monostearate are more preferable.

The content of the above-mentioned surfactant(s) (C) in the solid composition of the invention is usually 1 to 20% by weight, preferably 2 to 15% by weight, and more preferably 3 to 10% by weight based on the total weight of the composition.

There is no limitation on the polyhydric alcohol (D) used in the solid composition of the invention insofar as it is cosmetically or pharmacologically acceptable. Mentioned as examples of the polyhydric alcohol (D) are glycerol; polyglycerol, such as diglycerol, triglycerol, tetraglycerol, and the like; alkanediols, such as ethylene glycol, diethylene glycol, polyethylene glycol, 1,3-butylene glycol, propylene glycol, dipropylene glycol, isoprene glycol, 1,2-pentanediol, 1,2-hexandiol, 1,2-octanediol, and the like; sugar alcohols, such as mannitol, sorbitol, maltitol, fructose, and the like. These polyhydric alcohols may be used alone or in combination. As the polyhydric alcohol (D), preferable are glycerol, diglycerol, ethylene glycol, diethylene glycol, polyethylene glycol, 1,3-butylene glycol, dipropylene glycol, isoprene glycol, and more preferable are glycerol, diglycerol, dipropylene glycol, and 1,3-butylene glycol.

The content of the above-mentioned polyhydric alcohol (D) in the solid composition of the invention is usually 5 to 30% by weight, preferably 10 to 30% by weight, and more preferably 15 to 25% by weight.

There is no limitation on the electrolyte (E) used in the invention insofar as it is cosmetically or pharmacologically acceptable. Specifically mentioned as examples of the electrolyte (E) are various substances that exhibit their physiological functions when applied to the skin and that can be added in externally-applied preparations, particularly, cosmetics and externally-applied pharmaceuticals or quasi-medical products. Specific examples of the electrolyte (E) include purine bases, pyrimidine bases, water soluble vitamins, derivatives of water soluble vitamins, amino acids, amino acid derivatives, salts thereof, etc.

In this specification, purine bases refer to purine per se and various purine derivatives having a purine nucleus as a skeleton. Examples of purine bases include adenine, guanine, their deaminated forms (hypoxanthine, xanthine), adenosine, guanosine, inosine, adenosine phosphates (adenosine 2'-phosphate, adenosine 3'-phosphate, adenosine 5'-phosphate, adenosine 5'-diphosphate, adenosine 5'-triphosphate, cyclic adenosine 3',5'-monophosphate (cAMP)), guanosine phosphates (guanosine 3'-phosphate, guanosine 5'-phosphate, guanosine 5'-diphosphate, and guanosine 5'-triphosphate), adenylosuccinic acid, xanthic acid, inosinic acid, flavine adenine dinucleotide (FAD), nicotinamide adenine dinucleotide (NAD), and the like.

The pyrimidine bases refer to pyrimidine per se and various pyrimidine derivatives having a pyrimidine nucleus as a skeleton. Examples of such pyrimidine bases include uracil nucleic acid-related substances, such as uracil, uridine, uridine phosphates [uridine monophosphates (uridine 5'-phosphate, uridine 3'-phosphate, and uridine 2'-phosphate), uridine diphosphates, uridine triphosphates, cyclic uridine phosphate, etc.], deoxyuridine, deoxyuridine phosphates [5'-deoxyuridine diphosphate (dUDP), 5'-deoxyuridine phosphate(dUMP), etc.], and the like; cytosine nucleic acid-related substances, such as cytosine, cytidine, cytidine phosphates [cytidine monophosphates (cytidine 5'-phosphate, cytidine 3'-phosphate, cytidine 2'-phosphate), cytidine triphosphate (CTP), cytidine diphosphate (CDP)], deoxycytidine, deoxycytidine phosphates (5'-deoxycytidine triphosphate (dCTP), 5'-deoxycytidine diphosphate (dCDP), 5'-deoxycytidylicacid (dCMP), etc.), and the like; and thymine, thymidine, thymidine phosphates [thymidylic acid monophosphates (TMP), thymidine diphosphates (TDP), thymidine triphosphates (TTP), etc.], orotic acid, orotidine 5'-phosphate, and the like.

Examples of water soluble vitamins and derivatives thereof include the vitamin B group, ascorbic acid, lipoic acid, and derivatives thereof. Specific examples of the vitamin B group and derivatives thereof include vitamin $B_1$ derivatives, vitamin $B_2$, vitamin $B_6$, vitamin $B_{12}$, vitamin $B_{13}$, biotin, pantothenic acid, niacin, folic acid, inositol, etc. Examples of the above-mentioned vitamin $B_1$ derivatives include thiamine, thiamine disulfide, fursultiamine, dicethiamine, bisbutitiamine, bisbentiamine, benfotiamine, thiamine monophosphate disulfide, cyclothiamine, octotiamine, prosultiamine, etc. Examples of ascorbic acid derivatives include sodium L-ascorbyl phosphate, disodium L-ascorbyl sulfate, ascorbyl 2-glucoside, ascorbyl glucosamine, L-dehydroascorbic acid, magnesium L-ascorbyl phosphate, etc.

Mentioned as examples of amino acids and derivatives thereof are amino acids, such as serine, glycine, asparagine, aspartic acid, lysine, arginine, threonine, cysteine, glutamic acid, pyrrolidone carboxylic acid, and the like and derivatives thereof.

Mentioned as examples of the above-mentioned various salts are alkali-metal-salts such as sodium salt, potassium salt, and the like; basic amino acid salts such as arginine, lysine, and the like; ammonium salt, triethanolamine salt, etc.

The above-mentioned electrolytes may be used alone or in combination.

Among the above-mentioned electrolytes (E), purine bases, water soluble vitamins, and derivatives of water soluble vitamins, and salts thereof are preferable in the invention because they can exhibit excellent physiological activities when applied to the skin. Among the above, adenosine 3',5'-cyclic phosphoric acid, adenosine monophosphate, adenosine diphosphate, adenosine triphosphate, and salts thereof are useful because they demonstrate the actions of improving the metabolism of the skin and promoting the turnover of the skin when applied to the skin.

From the viewpoint of effectively demonstrating the action of improving skin pigmentation and preventing skin aging, it is more desirable to combine, as the electrolyte (E) in the solid composition of the invention, the component(s) (E-1) and the component(s) (E-2) as follows:

preferably, a combination of at least one selected from the group (E-1) consisting of purine bases and salts thereof and at least one selected from the group (E-2) consisting of water soluble vitamins and derivatives thereof;

more preferably, a combination of at least one selected from the group (E-1) consisting of adenosine 3',5'-cyclic phosphoric acid, adenosine monophosphate, adenosine diphosphate, adenosine triphosphate, and salts thereof and at least one selected from the group (E-2) consisting of ascorbic acid, derivatives thereof, and salts thereof;

still more preferably, a combination of at least one selected from the group (E-1) consisting of adenosine monophosphates and salts thereof and at least one selected from the group (E-2) consisting of ascorbyl 2-glucoside and salts thereof.

When the above-mentioned components (E-1) and (E-2) are combined as the electrolyte (E), the proportion of the component (E-2) is, for example, 0.5 to 1000 parts by weight, preferably 5 to 500 parts by weight, and more preferably 50 to 500 parts by weight based on 100 parts by weight of the component(s) (E-1). When the proportion is in the above range, the above-described actions can be demonstrated more effectively.

The solid composition of the invention comprising, as the electrolyte (E), the above-mentioned suitable compound(s) or the combination thereof is free from disadvantages (e.g., no solidification, bad feel when used, poor demonstration of physiological functions, etc.) produced when such electrolytes are applied to oil-in-water emulsions of conventional formulae and can be given with advantageous effects when formed into preparations.

The content of electrolyte mixed with the solid composition of the invention is not limited insofar as the amount is suitable for the electrolyte to demonstrate its intended effect (hereinafter referred to as an effective amount). Specifically, the content varies depending on the kind of electrolyte to be used, and is, for example, usually 0.1 to 20% by weight, preferably 1 to 15% by weight, and more preferably 3 to 10% by weight based on the total amount of the composition. The solid composition of the invention can maintain a good feel when used and a stable solid state even though an effective amount of electrolyte is contained therein as described above.

When the component(s) (E-1) is combined with the component(s) (E-2) as the electrolyte (E) as described above, the content of the component(s) (E-1) is 0.05 to 10% by weight and the content of the component(s) (E-2) is 0.05 to 10% by weight; preferably the content of the component(s) (E-1) is 0.1 to 7% by weight and the component(s) (E-2) is 0.5 to 10% by weight; and more preferably, the component(s) (E-1) is 0.5 to 6% by weight and the component (E-2) is 1 to 10% by weight, based on the total amount of the composition.

The solid composition of the invention contains water (F) as an essential ingredient. As the water (F), any of distilled water, ion-exchanged water, and sterilized water may be used. The content of the water (F) in the solid composition of the invention is usually 10 to 50% by weight, preferably 10 to 30% by weight, and more preferably 10 to 25% by weight based on the total amount of the composition. In the solid composition of the invention, the water (F) is preferably contained in a proportion of 20 to 60 parts by weight, preferably 20 to 50 parts by weight, and more preferably 20 to 40 parts by weight based on the total amount of 100 parts by weight of the solid oil(s) (A) and liquid oil(s) (B).

The solid composition of the invention can contain, other than the above-mentioned components, various known components such as UV absorbers, antioxidants, bactericides, anti-inflammatory agents, antiseptics, perfumes, colorants, and the like, in particular known components added to externally-applied compositions to be applied to the skin such as cosmetics, externally-applied pharmaceuticals or quasi-medical products, and the like insofar as the effects of the invention are not adversely affected.

The solid composition of the invention is used as transdermal or transmucosal preparations, such as cosmetics or externally-applied medical pharmaceuticals (including externally-applied quasi-medical products) that can exhibit physiological functions based on the action of the electrolyte contained in the composition.

The solid composition of the invention is not limited in shape insofar as it can be locally applied to the skin or mucosa, and a stick form can be mentioned as a preferable example of a suitable shape. The solid composition of the invention, when formed into a stick-like preparation, is suitably used as lip preparations, preparations to be partially applied to the skin, especially to the face, etc. When the composition is formed into a stick shape, the dimension is not limited. The composition is usually formed into a cylindrical shape having a diameter of 7 to 30 mm and a height of about 20 to 50 mm. In order to solidify the composition into a stick shape, it is desirable that the solid composition is self supportable. The "self supportable" means that the composition can retain its own shape without supporting the sides by putting it in a container or the like. Specifically, it means that when the composition having a cylindrical shape with a diameter of 10 mm and a height of 40 mm stands vertically on a base at a temperature of 30° C. and 60% relative humidity, the composition can maintain its own shape for at least 1 hour.

The solid composition of the invention can be prepared by a usual preparation method of a solid-like oil-in-water emulsion.

EXAMPLES

Hereinafter, the present invention will be explained with reference to Examples and Test Examples, but is not limited thereto.

Example 1

| Stick preparation for lips (lipstick) | |
|---|---|
| | (% by weight) |
| 1. liquid paraffin | 13.50 |
| 2. 2-hexyldecyl isostearate | 13.00 |
| 3. methyl polysiloxane | 0.50 |
| 4. candelilla wax | 13.50 |
| 5. hydrogenated jojoba oil | 8.00 |
| 6. lipophilic glycerol monostearate | 3.00 |
| 7. stearyl glycyrrhetinate | 0.10 |
| 8. polyoxyethylene hydrogenated castor oil (30E.O.) | 0.50 |
| 9. maltitol hydroxyalkyl (12,14) ether | 3.00 |
| 10. decaglycerol monostearate | 1.00 |
| 11. sodium N-stearoyl L-glutamate | 0.50 |
| 12. concentrated glycerol | 16.00 |
| 13. 1,3-butylene glycol | 6.00 |
| 14. L-ascorbyl 2-glucoside | 2.00 |
| 15. disodium adenosine monophosphate | 3.00 |
| 16. purified water | balance |
| | 100% by weight |

Components 1 to 8 were melted under stirring at 80° C. to prepare an oil phase, and separately, components 9 to 16 were dissolved under stirring at 80° C. to prepare an aqueous phase. Subsequently, the oil phase was added to the aqueous phase to form an emulsion. The emulsion was poured into a lipstick die, followed by cooling to thereby provide a lipstick consisting of an oil-in-water emulsion (cylinder 10 mm in diameter and 40 mm in height).

Example 2

| Stick preparation for skin | |
|---|---|
| | (% by weight) |
| 1. squalane | 8.50 |
| 2. cetyl 2-ethylhexanate | 12.00 |
| 3. ceresin | 20.00 |
| 4. hydrogenated jojoba oil | 8.00 |
| 5. lipophilic glycerol monostearate | 3.00 |
| 6. tocopherol | 0.05 |
| 7. polyoxyethylene hydrogenated castor oil (30E.O.) | 1.00 |
| 8. sucrose stearate | 3.00 |
| 9. decaglycerol monostearate | 1.00 |
| 10. 2-alkyl-N-carboxymethyl-N-hydroxyethyl imidazolinium betaine | 1.00 |
| 11. concentrated glycerol | 16.00 |
| 12. 1,3-butylene glycol | 6.00 |
| 13. L-ascorbyl 2-glucoside | 2.00 |
| 14. adenosine monophosphate disodium | 3.00 |
| 15. purified water | balance |
| | 100% by weight |

Components 1 to 7 were melted under stirring at 80° C. to prepare an oil phase, and separately, components 8 to 15 were dissolved under stirring at 80° C. to prepare an aqueous phase. Subsequently, the oil phase was added to the aqueous phase to form an emulsion. The emulsion was poured into a lipstick die, followed by cooling to thereby provide a lipstick consisting of an oil-in-water emulsion (cylinder 10 mm in diameter and 40 mm in height).

Example 3

| Stick preparation for moisturization | |
|---|---|
| 1. liquid paraffin | 13.50 |
| 2. 2-hexyldecyl isostearate | 13.50 |
| 3. methyl polysiloxane | 0.50 |
| 4. candelilla wax | 8.00 |
| 5. carnauba wax | 5.00 |
| 6. hydrogenated jojoba oil | 5.00 |
| 7. lipophilic glycerol monostearate | 3.00 |
| 8. polyoxyethylene hydrogenated castor oil (60E.O.) | 0.50 |
| 9. sucrose stearate | 3.00 |
| 10. decaglycerol monostearate | 1.00 |
| 11. diglycerol | 10.00 |
| 12. dipropylene glycol | 15.00 |
| 13. trimethylglycine | 5.00 |
| 14. L-ascorbic acid 2-glucoside | 2.00 |
| 15. adenosine monophosphate disodium | 3.00 |
| 16. purified water | balance |
| | 100% by weight |

Components 1 to 8 were melted under stirring at 80° C. to prepare an oil phase, and separately, components 9 to 16 were dissolved under stirring at 80° C. to prepare an aqueous phase. Subsequently, the oil phase was added to the aqueous phase to form an emulsion. The emulsion was poured into a lipstick die and followed by cooling, providing a lipstick consisting of an oil-in-water emulsion (cylinder 10 mm in diameter and 40 mm in height).

Test Example 1

The lipstick obtained in Example 1 was evaluated for the action and effects on the lips by the following method and under the following conditions.
<Experimental Conditions and Method>
1. Subject
Nine healthy adult men (33 to 52 years old, average: 42.9 years old) having no disease on the skin to be tested were selected.
2. Test Sample
The lipstick obtained in Example 1 was used as a test sample.
3. Test Method
1) Determination of Test Area
The test sample was thoroughly applied to the upper and lower lips. Right and left sections facing across the median line of the mucosa transition part at the boundary between the mucosa and skin of the lower lip were tested.
2) Measurement
Melanin index and softness were evaluated and evaluation was performed using the method described below. Measurement was performed after the test area was washed with a soap (trade name: Kao white, produced by Kao Corp.), and then the subjects were habituated in an environment control room (a temperature of 20° C. and 50% relative humidity) for 30 minutes.
Measurement of Melanin Index
The melanin index of the test area on the right side of the median line was measured every two weeks using a Mexameter (Courage+Khazaka Electronics GmbH). According to the device, three lights having different wavelengths (568, 660, and 880 nm) were directed to the skin, and, for measurement of the melanin index, the reflectance of each of the reflected lights (660 and 880 nm) from the skin was measured, thereby calculating the melanin index.

Skin Softness

The skin softness of the test area on the left side of the median line was measured using a tactile sensor Venustron (AXIOM). The measurement was performed at a probe velocity of 2 mm/sec and probe depth of 5 mm. At the time of analysis, the Tactile Δf(Hz) at a pressure of 6 g was read to determine the softness. The tactile sensor Venustron is a device that determines skin softness by bringing a probe that vibrates at a constant frequency into contact with a test subject and measuring the change Δf(Hz) in frequency. When the test subject is harder, the Δf becomes higher (change in the positive direction), while when the test subject is softer, the Δf becomes smaller (change in the negative direction).

3) Applying Method and Applying Period

The subjects were forbidden from applying cosmetic materials, medical or quasi medical drugs to the lips for at least two weeks so as to measure values before application of the test sample. The lips were washed and values before application were measured.

The test sample was thoroughly applied back and forth twice to each of the upper and lower lips in one application. The test sample was, in principle, applied to the skin at least 3 times per day after breakfast, lunch, and supper and applied in cases when the applied lipstick come off. Applications were continuously performed for 56 days. Applications were performed with frequencies higher than usual application frequencies of common lipsticks. During the test period, subjects were forbidden from stimulating the application area with a cloth, towel, etc., applying to the lips, cosmetics that may adversely affect the test, and sun tanning.

4) Data Processing Method

The measured values for every measurement were averaged and the change with time was analyzed. The significant difference of the melanin index was analyzed with the randomized blocks method (Dunnett) relative to the value before application as a control. With respect to softness, the significant difference between the value before application and the value when application was complete (eight weeks after application) was analyzed by paired t tests.

<Test Results>

FIG. 1 shows the change with time in melanin index during the test period. The melanin index shows that the higher the value, the larger the amounts of melanin. The melanin index when the test started was 81.6 and the melanin index when the test was complete was 42.9. This shows that the melanin index of the lower lip decreased by 38.8 through the application of the test sample for eight weeks. This decrease also had a statistically significant difference ($p<0.01$).

Figure 2:
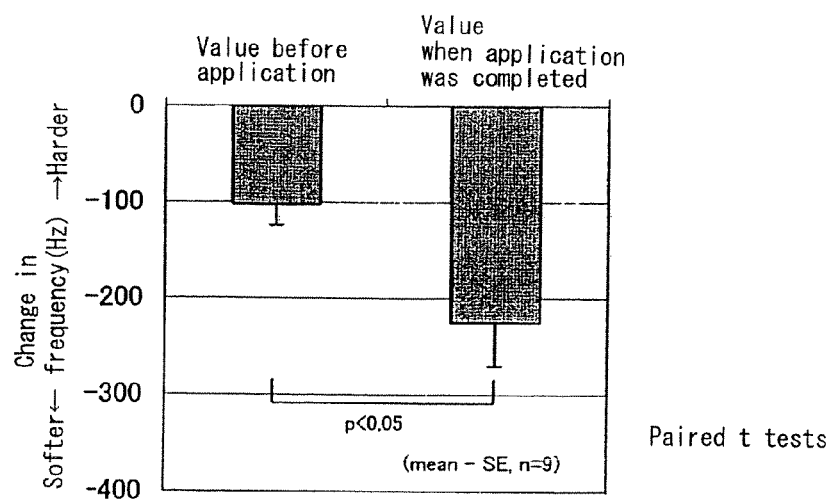
FIG. 2 is a graph showing the index of the softness of lips (frequency change, Hz) after the lipstick obtained in Example 1 is applied to the lips for 56 days.

FIG. 2 shows examination results of the softness of the lips measured when the test started and was complete. In FIG. 2, the change in frequency shows that the lips are softer as the change in frequency moves towards the negative direction. As shown in FIG. 2, the change in frequency (softness of the lower lip) when the test started was −102.3 Hz and the change in frequency when the test was complete was −226.0 Hz. This shows that the softness was improved when the test was complete. This difference was also statistically significant.

Test Example 2

Evaluation of Stability and Feel when Used

The feel when used and stability were examined using the lipstick obtained in Example 1 by the following method.

<Test Method>

1. Storage Conditions

The water-soluble stick (Example 1) was stored while being charged in a container for one month under the following conditions:

40° C./75% RH (storage condition 1),

25° C./65% RH (storage condition 2),

−5° C./no humidity control (storage condition 3), a cycle (1 cycle in a day: −5 to 40° C.)/no humidity control (storage condition 4). The indications of the above-mentioned storage conditions show (temperature conditions: ° C.)/(relative humidity: % RH). This test was conducted using three lipsticks for each condition (n=3).

2. Evaluation Items

The lipsticks before and after storage were evaluated for cracking, discoloration, odor, and feel when used.

<Test Results>

The obtained results are shown in Table 1. As shown in Table 1, the lipsticks showed no abnormalities in their appearances such as, discoloration, odor, cracking, etc. after one month storage under all of the test conditions. There were no problems in the feel when used. The above-described results show that the lipstick of the invention is a preparation having stable appearance and feel when used although it is in the form of an oil-in-water.

TABLE 1

|  | Evaluation Items | Storage condition 1 | Storage condition 2 | Storage condition 3 | Storage condition 4 |
|---|---|---|---|---|---|
| Before storage | Cracking | + | + | + | + |
|  | Discoloration | + | + | + | + |
|  | Odor | + | + | + | + |
|  | Feel when used | No uncomfortable feelings during use | No uncomfortable feelings during use | No uncomfortable feelings during use | No uncomfortable feelings during use |
| After storage | Cracking | + | + | + | + |
|  | Discoloration | + | + | + | + |
|  | Odor | + | + | + | + |
|  | Feel when used | No uncomfortable feelings during use | No uncomfortable feelings during use | No uncomfortable feelings during use | No uncomfortable feelings during use |

Note:
In Table 1, "+" in the column of "before storage" shows no abnormalities, and "+" in the column of "after storage" shows no abnormalities and no differences compared with the conditions before storage.

INDUSTRIAL APPLICABILITY

In general, oil-in-water emulsions in which an electrolyte is dissolved in an aqueous phase are hard to solidify. Even if such an emulsion can be solidified, the resultant solid is sticky and difficult to spread on the skin, resulting in a bad feel when used. However, the solid composition of the invention can achieve good solidification, stable solid state, stable emulsified state, inhibition of moisture evaporation, improvement in the permeability of the electrolyte component in the skin, improvement in a feel when used, etc., by containing a combination of components (A) to (F). Therefore, the solid composition of the invention has favorable smoothness and softness, resulting in an excellent feel when used, and can stably maintain the solid state of an oil-in-water emulsion while effectively retaining the electrolytic effect.

In particular, solid oil-in-water emulsions of conventional formulae are extremely difficult to achieve stable solidification, good feel when used, and demonstration of excellent physiological functions by containing a combination of an effective amount of at least one selected from the group (E-1) consisting of purine bases and salts thereof and an effective amount of at least one selected from the group (E-2) consisting of water soluble vitamins and derivatives thereof. In contrast, the invention can prepare a solid oil-in-water emulsion that is completely free from the above disadvantages while containing an effective amount of the above components (E-1) and (E-2).

The solid composition of the invention has a good feel when used also in that the solid composition has a favorable feeling to the skin and is less irritating to the skin. The solid composition of the invention, when formulated in the shape of a stick, has excellent portability and can be locally applied to the skin of a human body, which makes it possible to keep the hands clean during use. Therefore, the stick shaped solid composition of the invention has both portability and convenience during use.

The invention claimed is:

1. A solid composition in the form of an oil-in-water emulsion comprising:
   at least one solid oil;
   at least one liquid oil;
   at least one non-ionic surfactant;
   at least one species of polyhydric alcohol selected from the group consisting of glycerol, diglycerol, ethylene glycol, diethylene glycol, polyethylene glycol, 1,3-butylene glycol, dipropylene glycol, and isoprene glycol;
   a plurality of electrolytes, wherein the plurality of electrolytes is a combination of (1) at least one first electrolyte selected from the group consisting of adenosine 3',5'-cyclic phosphoric acid, adenosine monophosphate, adenosine diphosphate, adenosine triphosphate, and salts thereof, and (2) at least one second electrolyte selected from the group consisting of ascorbic acid, vitamin B1 (thiamin), ascorbic acid derivatives, vitamin B1 (thiamin) derivatives, and salts thereof; and
   water; wherein
   (i) the total concentration of solid oil in the solid composition is 15% to 30% by weight;
   (ii) the total concentration of liquid oil in the solid composition is 15% to 30% by weight;
   (iii) the concentration of water in the solid composition is 10% to 30% by weight;
   (iv) the plurality of electrolytes is present in the solid composition at a concentration of 1% to 15% by weight;
   (v) the water is present in a proportion of 20 to 60 parts by weight based on the total amount of 100 parts by weight of the solid oil and the liquid oil;
   (vi) the total concentration of nonionic surfactant in the solid composition is 3% to 10% by weight; and
   (vii) the total concentration of the at least one species of polyhydric alcohol in the solid composition is 15% to 25% by weight.

2. The solid composition according to claim 1, wherein the at least one second electrolyte comprises ascorbic acid, an ascorbic acid derivative, or a salt thereof.

3. The solid composition according to claim 2, wherein the at least one first electrolyte comprises adenosine monophosphate or a salt thereof.

4. The solid composition according to claim 1, wherein the composition is a cosmetic.

5. The solid composition according to claim 1, wherein the composition is an externally-applied pharmaceutical.

6. The solid composition according to claim 1, wherein the composition is in a lipstick form.

7. The solid composition according to claim 1, wherein the at least one non-ionic surfactant comprises lipophilic glycerol monostearate.

8. The solid composition according to claim 1, wherein the at least one non-ionic surfactant comprises polyoxyethylene hydrogenated castor oil.

9. The solid composition according to claim 1, wherein the at least one non-ionic surfactant comprises both lipophilic glycerol monostearate and polyoxyethylene hydrogenated castor oil.

10. The solid composition according to claim 1, wherein the at least one species of polyhydric alcohol comprises both of the following two species of polyhydric alcohol: glycerol and 1,3-butylene glycol.

11. The solid composition according to claim 1, wherein the at least one species of polyhydric alcohol comprises both of the following two species of polyhydric alcohol: diglycerol and dipropylene glycol.

12. The solid composition according to claim 1, wherein the at least one first electrolyte comprises adenosine monophosphate disodium, and wherein the at least one second electrolyte comprises L-ascorbic acid 2-glucoside.

13. The solid composition according to claim 1, wherein the at least one solid oil comprises hydrogenated jojoba oil.

14. The solid composition according to claim 13, wherein the at least one solid oil further comprises one or more of the following three species of solid oil: candelilla wax, ceresin, and carnauba wax.

15. The solid composition according to claim 1, wherein:
   (a) the at least one non-ionic surfactant comprises lipophilic glycerol monostearate;
   (b) the at least one species of polyhydric alcohol comprises at least two of the following four species of polyhydric alcohol: glycerol, diglycerol, dipropylene glycol, and 1,3-butylene glycol; and
   (c) the at least one solid oil comprises hydrogenated jojoba oil.

16. The solid composition according to claim 15, wherein the at least one first electrolyte comprises adenosine monophosphate disodium, and wherein the at least one second electrolyte comprises L-ascorbic acid 2-glucoside.

17. The solid composition according to claim 15, wherein the at least one solid oil further comprises one or more of the following three species of solid oil: candelilla wax, ceresin, and carnauba wax.

18. The solid composition according to claim 16, wherein the at least one solid oil further comprises one or more of the following three species of solid oil: candelilla wax, ceresin, and carnauba wax.

* * * * *